United States Patent
Sandanayaka et al.

(10) Patent No.: US 7,576,102 B2
(45) Date of Patent: *Aug. 18, 2009

(54) BIARYL SUBSTITUTED NITROGEN CONTAINING HETEROCYCLE INHIBITORS OF LTA4H FOR TREATING INFLAMMATION

(75) Inventors: Vincent Sandanayaka, Northboro, MA (US); Jasbir Singh, Naperville, IL (US); Mahnaz Keyvan, Plainfield, IL (US); Michael David Krohn, Romeoville, IL (US); Mark E. Gurney, Grand Rapids, MI (US)

(73) Assignee: deCODE genetics ehf, Reykjavik (IS)

( * ) Notice: Subject to any disclaimer, the term of this patent is extended or adjusted under 35 U.S.C. 154(b) by 0 days.

This patent is subject to a terminal disclaimer.

(21) Appl. No.: 11/462,296

(22) Filed: Aug. 3, 2006

(65) Prior Publication Data

US 2007/0142432 A1   Jun. 21, 2007

Related U.S. Application Data

(60) Provisional application No. 60/752,274, filed on Dec. 21, 2005.

(51) Int. Cl.
*A61K 31/454* (2006.01)
*A61K 31/4025* (2006.01)
*A61K 31/4015* (2006.01)
*C07D 211/54* (2006.01)
*C07D 207/24* (2006.01)

(52) U.S. Cl. .................. 514/317; 514/326; 514/422; 514/424; 546/207; 546/216; 548/517; 548/544

(58) Field of Classification Search .................. 546/192, 546/207, 216; 548/543, 579, 517, 544; 514/192, 514/317, 326, 422, 424
See application file for complete search history.

(56) References Cited

U.S. PATENT DOCUMENTS 5,561,145 A   10/1996   Prucher et al.
6,756,400 B2 *   6/2004   Chinn et al. ................. 514/422
7,402,684 B2 *   7/2008   Sandanayaka et al. ....... 548/574

FOREIGN PATENT DOCUMENTS

| JP | 2004-010513 | | 1/2004 |
| JP | 2004-010514 | | 1/2004 |
| JP | 2004-262890 | | 9/2004 |
| WO | WO 9413291 | * | 6/1994 |
| WO | WO 95/24390 | | 9/1995 |
| WO | 03/022821 | | 3/2003 |
| WO | WO 2005/012296 | | 2/2005 |
| WO | WO 2006064033 | * | 6/2006 |

OTHER PUBLICATIONS

CA Registry No. 183170-13-0, entry date into Registry file on STN is Nov. 19, 1996.*
Grenier et al, CA 67:2990, 1996.*
Aono et al, CA 125:328725, 1998.*
Pruecher et al. CAS Accession No. 1995:501323, Year 1995.*
International Search Report for PCT/US2006/030526.

* cited by examiner

*Primary Examiner*—Rei-Tsang Shiao
*Assistant Examiner*—Joseph R Kosack
(74) *Attorney, Agent, or Firm*—Heslin Rothenberg Farley & Mesiti P.C.

(57) ABSTRACT

The present invention relates to a chemical genus of biaryl substituted nitrogen-attached heterocycles that are inhibitors of LTA4H (leukotriene A4 hydrolase). The compounds have the general formula:

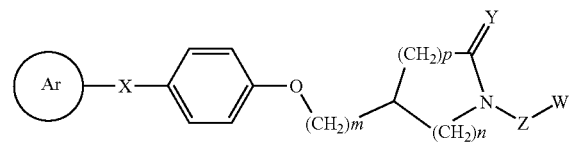

They are useful for the treatment and prevention and prophylaxis of inflammatory diseases and disorders.

11 Claims, No Drawings

BIARYL SUBSTITUTED NITROGEN CONTAINING HETEROCYCLE INHIBITORS OF LTA4H FOR TREATING INFLAMMATION

CROSS-REFERENCE TO RELATED APPLICATION

This application claims priority from U.S. Provisional Application Ser. No. 60/752,274, filed Dec. 21, 2005, the entire contents of which are incorporated herein by reference.

FIELD OF THE INVENTION

The present invention relates to a chemical genus of biphenyl nitrogen containing heterocyclic derivative inhibitors of LTA4H (leukotriene A4 hydrolase) useful for the treatment and prevention and prophylaxis of inflammatory diseases and disorders.

BACKGROUND OF THE INVENTION

The end products of the leukotriene pathway are potent inflammatory lipid mediators derived from arachidonic acid. They can potentially contribute to development of atherosclerosis and destabilization of atherosclerotic plaques through lipid oxidation and/or proinflammatory effects. As described elsewhere, a gene on chromosome 13q12 has been identified as playing a major role in myocardial infarction (MI), [Helgadottir et al., Nature Genetics doi: 10.1038/ng1311, 8 Feb. 2004]. This gene (ALOX5AP), herein after referred to as an MI disease gene, comprises nucleic acid that encodes 5-lipoxygenase activating protein (FLAP), herein after referred to as FLAP. DNA variants in the FLAP gene increase risk for myocardial infarction by 1.8 fold and for stroke by 1.7 fold. The leukotriene pathway, through FLAP, leads to the production of leukotriene B4 by the enzyme leukotriene A4 hydrolase (LTA4H). Leukotriene B4 is one of the most potent chemokine mediators of arterial inflammation. Particular DNA variants in the gene encoding LTA4H also elevate risk for MI and stroke, as described elsewhere [Hakonarsson et al., J. Am. Med. Assoc. 293, 2245-2256 (2005)]. Individuals with a prior history of MI produce more leukotriene B4 when their isolated neutrophils are stimulated with ionomycin. Increased LTB4 production is particularly marked in male patients with a prior history of MI who carry risk variants in the FLAP gene [Helgadottir et al.]. The treatment (prophylactic and/or therapeutic) of certain diseases and conditions (e.g., MI, acute coronary syndrome (ACS), stroke, atherosclerosis) associated with FLAP or with LTA4H can be accomplished by inhibiting LTA4H. Inhibiting LTA4H is advantageous for methods of treatment for MI or susceptibility to MI; for ACS (e.g., unstable angina, non-ST-elevation myocardial infarction (NSTEMI) or ST-elevation myocardial infarction (STEMI)); for decreasing risk of a second MI; for stroke (including transient ischemic attack) or susceptibility to stroke; for atherosclerosis, such as for patients requiring treatment (e.g., angioplasty, stents, coronary artery bypass graft) to restore blood flow in coronary arteries, such as patients requiring treatment for peripheral vascular disease including peripheral occlusive arterial disease, critical limb ischemia (e.g., gangrene, ulceration), and intermittent claudication to restore blood flow in the lower limbs; for atherosclerotic reno-vascular disease; for abdominal aortic aneurysm; and/or for decreasing leukotriene synthesis (e.g., for treatment of MI).

US Patent Application Publication No. 20050043378 and 20050043379, relate to benzoxazol-2-yl, benzothiazol-2-yl and 1H-benzimidazol-2-yl compounds and derivatives thereof useful as leukotriene A4 hydrolase (LTA4H) inhibitors in treating inflammation and disorders associated with inflammation. These disclosures are incorporated herein by reference as they relate to utility.

SUMMARY OF THE INVENTION

The present invention relates to compounds exhibiting LTA4H enzyme inhibition, having general formula:

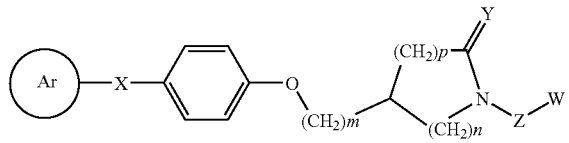

wherein
Ar is selected from the group consisting of aryl, aryl substituted with from one to three substituents independently selected from the group consisting of halogen, loweralkyl, loweracyl, loweralkoxy, fluoroloweralkyl, fluoroloweralkoxy, formyl, cyano, benzyl, benzyloxy, phenyl, substituted phenyl, heteroaryl, heterocyclylalkyl and nitro; heteroaryl, and heteroaryl substituted with from one to three substituents independently selected from the group consisting of halogen, loweralkyl, loweracyl, loweralkoxy, fluoroloweralkyl, fluoroloweralkoxy, formyl, cyano, sulphonamide, amido, phenyl, heteroaryl, heterocyclylalkyl and nitro;

X is selected from the group consisting of direct bond, O, SO, $S(O_2)$, $NR^{10}$, $CH_2$, $CF_2$, $CH_2CH_2$, $CH_2NH$, $NHCH_2$, CH=CH, C=O, $CH_2C$=O; $CR^{1a}R^{1b}$ $OCR^{1a}R^{1b}$ and $CR^{1a}R^{1b}O$;

$R^{10}$ is selected separately in each occurrence from the group consisting of H and lower alkyl;

$R^{1a}$ and $R^{1b}$ are selected from the group consisting of H and lower alkyl, or $R^{1a}$ and $R^{1b}$ taken together may form a 3-6 membered ring, which may optionally contain a heteroatom chosen from O, S, SO, $SO_2$, and $NR^{10}$;

m is zero, 1 or 2;
n is an integer chosen from 1, 2, or 3;
p is an integer from 0-3;
Y is H,H; O; or H,$R^3$;
$R^3$ is lower alkyl;
taken together ZW is H or
Z is $(CH_2)_{1-10}$; in which one or two $(CH_2)$ may optionally be replaced by a $C_3$-$C_6$ carbocycle, a $C_3$-$C_6$ heterocycle, —O—, —$NR^{10}$—, —SO—, —$S(O)_2$—, —C(=O)— or —C=O(NH)—, provided that said —O—, —$NR^{10}$—, —SO—, —$S(O)_2$—, —C(=O)— or —C=O(NH)— are not at the point of attachment to nitrogen and are separated by at least one —$(CH_2)$—;

W is selected from acyl, hydroxyl, carboxyl, amino, carboxamido, sulphonamide, aminoacyl, —COOalkyl, —CHO, —C(O)fluororalkyl, —C(O)$CH_2$C(O)Oalkyl, —C(O)$CH_2$C(O)Ofluoroalkyl, —SH, —C(O)NH(OH), —C(O)N(OH)R, —N(OH)C(O)OH, —N(OH)C(O)$R^4$, heterocyclyl, substituted aryl, and substituted heterocyclyl; and $R^4$ is selected from the group consisting of H and lower alkyl.

In a second aspect the invention relates to a pharmaceutical composition comprising a pharmaceutically acceptable carrier and a therapeutically effective amount of a compound as described herein.

In a third aspect, the invention relates to methods for the treatment and prevention or prophylaxis of a disease, condition or disorder associated with leukotriene A4 hydrolase. The methods comprise administering to a mammal a therapeutically effective amount of a compound described above. The disease or condition may be related to allergic, acute or chronic inflammation. The disease may be for example contact and atopic dermatitis, arthritis, allergic rhinitis, asthma or an autoimmune diseases such as Crohn's disease, psoriasis, ulcerative colitis, hypercholesterolemia, inflammatory bowel disease, multiple sclerosis, ankylosing spondylitis, and the like. Similarly, the compounds defined above can be used in preventing recurring inflammatory attacks. The compounds are also useful for treating and preventing atherosclerosis, thrombosis, stroke, acute coronary syndrome, stable angina, peripheral vascular disease, critical leg ischemia, intermittent claudication, abdominal aortic aneurysm and myocardial infarction.

DETAILED DESCRIPTION OF THE INVENTION

Throughout this specification the substituents are defined when introduced and retain their definitions.

In one aspect the invention relates to biphenyl heterocycle derivatives useful as LTA4H enzyme inhibitors, having the general formula:

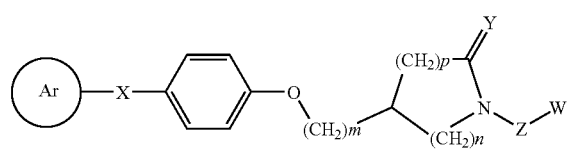

In some embodiments, Ar is phenyl or substituted phenyl and m is zero. These embodiments are illustrated by the formula:

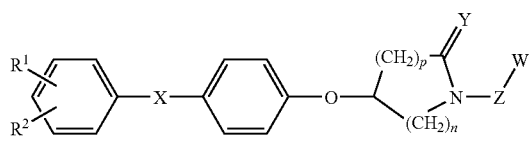

wherein $R^1$ and $R^2$ are independently chosen from hydrogen, halogen, loweralkyl, loweracyl, loweralkoxy, fluoroloweralkyl, fluoroloweralkoxy, formyl, cyano, benzyl, benzyloxy, sulphonamide, amido, phenyl, substituted phenyl, heteroaryl, heterocyclylalkyl and nitro;

or $R^1$ and $R^2$ taken together may form a 5-6 membered ring, which may optionally contain an oxygen.

In some embodiments, n is 1 or 2, and p is 1 or 2;

ZW is H or

Z is $(CH_2)_{1-10}$;

Y is H,H; O; or H and $R^3$; and

W is selected from acyl, hydroxyl, carboxyl, amino, carboxamido, aminoacyl, and —COOalkyl.

Examples of the substituent Y can be represented by the structures below wherein the wavy lines indicate ring bonds:

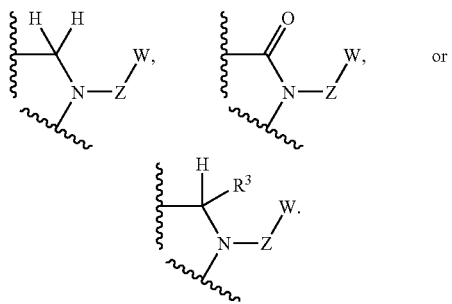

In some embodiments, n is 1 or 2, and p is 1 or 2;

ZW is H or

Z is $(CH_2)_{1-10}$, in which one or two $(CH_2)$ may optionally be replaced by a $C_3$-$C_6$ carbocycle or a $C_3$-$C_6$ heterocycle;

Y is H,H; O; or H,$R^3$; and

W is selected from acyl, hydroxyl, carboxyl, amino, carboxamido, aminoacyl, and —COOalkyl.

Examples where one or two $(CH_2)$ linkers of Z are optionally replaced by a $C_3$-$C_6$ carbocycle or a $C_3$-$C_6$ heterocycle include but are not limited to the structures below wherein the wavy lines indicate ring bonds:

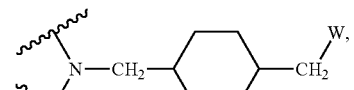

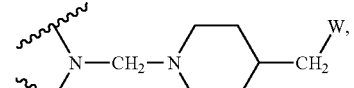

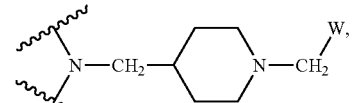

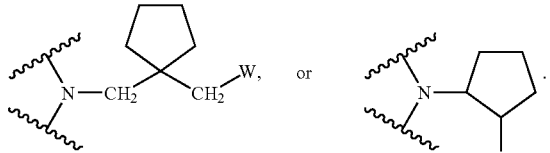

In some embodiments, p is one and Y is H,H. These embodiments are illustrated by the formula:

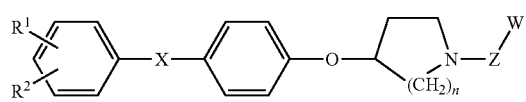

wherein $R^1$ and $R^2$ are chosen from hydrogen, trifluoromethyl, methyl, methoxy, halogen, phenyl, cyano and nitro, or $R^1$ and $R^2$ taken together may form a 5-6 membered ring, which ring may optionally contain an oxygen;

X is chosen from —O— and —CH$_2$—;
ZW is H or
Z is (CH$_2$)$_{1-3}$ and
W is COOH.

In another aspect the present invention provides a pharmaceutical composition comprising a pharmaceutically acceptable carrier and a therapeutically effective amount of at least one compound as described above.

Methods of the invention parallel the compositions and formulations. The methods comprise administering to a patient in need of treatment a therapeutically effective amount of a compound according to the invention.

The present invention provides a method for inhibiting leukotriene A4 hydrolase comprising contacting the LTA4H enzyme with a therapeutically effective amount of a compound according to the general formula

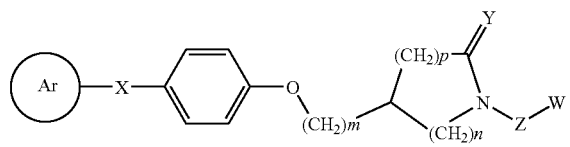

Furthermore, the present invention provides a method for treating a disorder associated with leukotriene A4 hydrolase comprising administering to a mammal a therapeutically effective amount of a compound or a salt, hydrate or ester thereof according to the general formula given above. It may be found upon examination that additional species and genera not presently excluded are not patentable to the inventors in this application. In either case, the exclusion of species and genera in applicants' claims are to be considered artifacts of patent prosecution and not reflective of the inventors' concept or description of their invention. The invention, in a composition aspect, is all compounds of the general formula above, except those that are in the public's possession. The invention, in a method aspect, is a method employing compounds of the general formula above, except those methods that are in the public's possession.

In some embodiments the disorder is associated with inflammation. In some embodiments the disorder is selected from allergic inflammation, acute inflammation and chronic inflammation.

Compounds of the genus represented by the general formula above are inhibitors of LTA$_4$H enzyme. As such they have utility in treating and preventing inflammatory diseases and disorders, as described above, particularly for such conditions as asthma, chronic obstructed pulmonary disease (COPD), atherosclerosis, rheumatoid arthritis, multiple sclerosis, hypercholoesterolemia, inflammatory bowel diseases (IBD; including Crohn's disease and ulcerative colitis), or psoriasis, which are each characterized by excessive or prolonged inflammation at some stage of the disease.

Recent research indicates that the compounds are also useful for treating and preventing atherosclerosis, thrombosis, stroke, acute coronary syndrome, stable angina, peripheral vascular disease, critical leg ischemia, intermittent claudication, abdominal aortic aneurysm and myocardial infarction atherosclerosis, thrombosis, stroke, acute coronary syndrome and myocardial infarct.

The compounds may be presented as salts. The term "pharmaceutically acceptable salt" refers to salts whose counter ion derives from pharmaceutically acceptable non-toxic acids and bases. Suitable pharmaceutically acceptable base addition salts for the compounds of the present invention include, but are not limited to, metallic salts made from aluminum, calcium lithium, magnesium, potassium, sodium and zinc or organic salts made from lysine, N,N-dialkyl amino acid derivatives (e.g. N,N -dimethylglycine, piperidine-1-acetic acid and morpholine-4-acetic acid), N,N'-dibenzylethylenediamine, chloroprocaine, choline, diethanolamine, ethylenediamine, meglumine (N-methylglucamine) and procaine. When the compounds contain a basic residue, suitable pharmaceutically acceptable base addition salts for the compounds of the present invention include inorganic acids and organic acids. Examples include acetate, benzenesulfonate (besylate), benzoate, bicarbonate, bisulfate, carbonate, camphorsulfonate, citrate, ethanesulfonate, fumarate, gluconate, glutamate, bromide, chloride, isethionate, lactate, maleate, malate, mandelate, methanesulfonate, mucate, nitrate, pamoate, pantothenate, phosphate, succinate, sulfate, tartrate, p-toluenesulfonate, and the like.

For convenience and clarity certain terms employed in the specification, examples and claims are described herein.

Alkyl is intended to include linear, branched, or cyclic hydrocarbon structures and combinations thereof Lower alkyl refers to alkyl groups of from 1 to 6 carbon atoms. Examples of lower alkyl groups include methyl, ethyl, propyl, isopropyl, butyl, s- and t-butyl and the like. Preferred alkyl groups are those of C$_{20}$ or below. Cycloalkyl is a subset of alkyl and includes cyclic hydrocarbon groups of from 3 to 8 carbon atoms. Examples of cycloalkyl groups include c-propyl, c-butyl, c-pentyl, norbornyl and the like.

C$_1$ to C$_{20}$ hydrocarbon includes alkyl, cycloalkyl, alkenyl, alkynyl, aryl, arylalkyl and combinations thereof Examples include phenethyl, cyclohexylmethyl, camphoryl, adamantyl and naphthylethyl.

Alkoxy or alkoxyl refers to groups of from 1 to 8 carbon atoms of a straight, branched, cyclic configuration and combinations thereof attached to the parent structure through oxygen. Examples include methoxy, ethoxy, propoxy, isopropoxy, cyclopropyloxy, cyclohexyloxy and the like. For the purposes of this application, alkoxy also includes methylenedioxy and ethylenedioxy. Lower-alkoxy refers to groups containing one to four carbons.

Alkoxyalkyl refers to ether groups of from 3 to 8 atoms of a straight, branched, cyclic configuration and combinations thereof attached to the parent structure through an alkyl. Examples include methoxymethyl, methoxyethyl, ethoxypropyl, and the like.

Alkoxyaryl refers to alkoxy substituents attached to an aryl, wherein the aryl is attached to the parent structure. Arylalkoxy refers to aryl substituents attached to an oxygen, wherein the oxygen is attached to the parent structure. Substituted arylalkoxy refers to a substituted aryl substituent attached to an oxygen, wherein the oxygen is attached to the parent structure.

Acyl refers to groups of from 1 to 8 carbon atoms of a straight, branched, cyclic configuration, saturated, unsaturated and aromatic and combinations thereof, attached to the parent structure through a carbonyl functionality. One or more carbons in the acyl residue may be replaced by nitrogen, oxygen or sulfur as long as the point of attachment to the parent remains at the carbonyl. Examples include acetyl, benzoyl, propionyl, isobutyryl, t-butoxycarbonyl, benzyloxycarbonyl and the like. Lower-acyl refers to groups containing one to four carbons.

Aryl and heteroaryl mean a 5- or 6-membered aromatic or heteroaromatic ring containing 0-3 heteroatoms selected from O, N, or S; a bicyclic 9- or 10-membered aromatic or heteroaromatic ring system containing 0-3 heteroatoms selected from O, N, or S; or atricyclic 13- or 14-membered aromatic or heteroaromatic ring system containing 0-3 heteroatoms selected from O, N, or S. The aromatic 6- to 14-membered carbocyclic rings include, e.g., benzene and naphthalene, and according to the invention benzoxalane and residues in which one or more rings are aromatic, but not all need be. The 5- to 10-membered aromatic heterocyclic rings include, e.g., imidazole, pyridine, indole, thiophene, benzopyranone, thiazole, furan, benzimidazole, quinoline, isoquinoline, quinoxaline, pyrimidine, pyrazine, tetrazole and pyrazole.

Arylalkyl refers to a substituent in which an aryl residue is attached to the parent structure through alkyl. Examples are benzyl, phenethyl and the like. Heteroarylalkyl refers to a substituent in which a heteroaryl residue is attached to the parent structure through alkyl. Examples include, e.g., pyridinylmethyl, pyrimidinylethyl and the like. Heterocyclylalkyl refers to a substituent in which a heterocyclyl residue is attached to the parent structure through alkyl. Examples include morpholinoethyl and pyrrolidinylmethyl.

Heterocycle means a cycloalkyl or aryl residue in which from one to three carbons is replaced by a heteroatom selected from the group consisting of N, O and S. The nitrogen and sulfur heteroatoms may optionally be oxidized, and the nitrogen heteroatom may optionally be quaternized. Examples of heterocycles include pyrrolidine, pyrazole, pyrrole, indole, quinoline, isoquinoline, tetrahydroisoquinoline, benzofuran, benzodioxan, benzodioxole (commonly referred to as methylenedioxyphenyl, when occurring as a substituent), benzo-[1,4]-dioxane (commonly referred to as ethylenedioxyphenyl, when occurring as a substitutent), tetrazole, morpholine, thiazole, pyridine, pyridazine, pyrimidine, thiophene, furan, oxazole, oxazoline, isoxazole, dioxane, tetrahydrofuran and the like. It is to be noted that heteroaryl is a subset of heterocycle in which the heterocycle is aromatic. Examples of heterocyclyl residues additionally include piperazinyl, 2-oxopiperazinyl, 2-oxopiperidinyl, 2-oxo-pyrrolidinyl, 2-oxoazepinyl, azepinyl, 4-piperidinyl, pyrazolidinyl, imidazolyl, imidazolinyl, imidazolidinyl, pyrazinyl, oxazolidinyl, isoxazolidinyl, thiazolidinyl, isothiazolyl, quinuclidinyl, isothiazolidinyl, benzimidazolyl, thiadiazolyl, benzopyranyl, benzothiazolyl, tetrahydrofuryl, tetrahydropyranyl, thienyl, benzothienyl, thiamorpholinyl, thiamorpholinylsulfoxide, thiamorpholinylsulfone, oxadiazolyl, triazolyl and tetrahydroquinolinyl.

An oxygen heterocycle is a heterocycle containing at least one oxygen in the ring; it may contain additional oxygens, as well as other heteroatoms. A sulphur heterocycle is a heterocycle containing at least one sulphur in the ring; it may contain additional sulphurs, as well as other heteroatoms. A nitrogen heterocycle is a heterocycle containing at least one nitrogen in the ring; it may contain additional nitrogens, as well as other heteroatoms. Oxygen heteroaryl is a subset of oxygen heterocycle; examples include furan and oxazole. Sulphur heteroaryl is a subset of sulphur heterocycle; examples include thiophene and thiazine. Nitrogen heteroaryl is a subset of nitrogen heterocycle; examples include pyrrole, pyridine and pyrazine. A saturated nitrogenous heterocycle is a subset of nitrogen heterocycle. Saturated nitrogenous heterocycle contain at least one nitrogen and may contain additional nitrogens, as well as other heteroatoms. Examples include pyrrolidine, pyrazolidine, piperidine, morpholine, and thiomorpholine.

Substituted alkyl, aryl, cycloalkyl, heterocyclyl etc. refer to alkyl, aryl, cycloalkyl, or heterocyclyl wherein up to three H atoms in each residue are replaced with halogen, haloalkyl, hydroxy, loweralkoxy, carboxy, carboalkoxy (also referred to as alkoxycarbonyl), carboxamido (also referred to as alkylaminocarbonyl), cyano, carbonyl, nitro, amino, alkylamino, dialkylamino, mercapto, alkylthio, sulfoxide, sulfone, acylamino, amidino, phenyl, benzyl, heteroaryl, phenoxy, benzyloxy, or heteroaryloxy.

The terms "halogen" and "halo" refer to fluorine, chlorine, bromine or iodine.

The term "hydroxamate" refers to hydroxamic acid and its salts and esters:

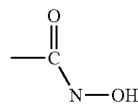

The term "prodrug" refers to a compound that is made more active in vivo. Activation in vivo may come about by chemical action or through the intermediacy of enzymes. Microflora in the GI tract may also contribute to activation in vivo.

It will be recognized that the compounds of this invention can exist in radiolabeled form, i.e., the compounds may contain one or more atoms containing an atomic mass or mass number different from the atomic mass or mass number usually found in nature. Radioisotopes of hydrogen, carbon, phosphorous, fluorine, and chlorine include $^{2}H$, $^{3}H$, $^{13}C$, $^{14}C$, $^{15}N$, $^{35}S$, $^{18}F$, and $^{36}Cl$, respectively. Compounds that contain those radioisotopes and/or other radioisotopes of other atoms are within the scope of this invention. Tritiated, i.e. $^{3}H$, and carbon-14, i.e., $^{14}C$, radioisotopes are particularly preferred for their ease in preparation and detectability. Radiolabeled compounds of formula $\Psi$ of this invention and prodrugs thereof can generally be prepared by methods well known to those skilled in the art. Conveniently, such radiolabeled compounds can be prepared by carrying out the procedures disclosed in the Examples and Schemes by substituting a readily available radiolabeled reagent for a non-radiolabeled reagent.

As used herein, and as would be understood by the person of skill in the art, the recitation of "a compound" is intended to include salts, solvates, co-crystals and inclusion complexes of that compound.

The term "solvate" refers to a compound of formula I in the solid state, wherein molecules of a suitable solvent are incorporated in the crystal lattice. A suitable solvent for therapeutic administration is physiologically tolerable at the dosage administered. Examples of suitable solvents for therapeutic administration are ethanol and water. When water is the solvent, the solvate is referred to as a hydrate. In general, solvates are formed by dissolving the compound in the appropriate solvent and isolating the solvate by cooling or using an antisolvent. The solvate is typically dried or azeotroped under ambient conditions. Co-crystals are combinations of two or more distinct molecules arranged to create a unique crystal form whose physical properties are different from those of its pure constituents. Pharmaceutical co-crystals have recently become of considerable interest for improving the solubility, formulation and bioavailability of such drugs as itraconazole [see Remenar el al. J. Am. Chem. Soc. 125, 8456-8457 (2003)] and fluoxetine. Inclusion complexes are described in Remington: The Science and Practice of Pharmacy 19$^{th}$ Ed. (1995) volume 1, page 176-177. The most commonly employed inclusion complexes are those with cyclodextrins, and all cyclodextrin complexes, natural and synthetic, with or without added additives and polymer(s), as described in U.S. Pat. Nos. 5,324,718 and 5,472,954, are specifically encompassed within the claims. The disclosures of Remington and the '718 and '954 patents are incorporated herein by reference.

The compounds described herein may contain asymmetric centers and may thus give rise to enantiomers, diastereomers, and other stereoisomeric forms. Each chiral center may be defined, in terms of absolute stereochemistry, as (R)— or (S)—. The present invention is meant to include all such possible isomers, as well as, their racemic and optically pure forms. Optically active (R)— and (S)— isomers may be prepared using chiral synthons or chiral reagents, or resolved using conventional techniques. The prefix "rac" refers to a racemate. When the compounds described herein contain olefinic double bonds or other centers of geometric asymmetry, and unless specified otherwise, it is intended that the compounds include both E and Z geometric isomers. The representation of the configuration of any carbon-carbon double bond appearing herein is selected for convenience only, and unless explicitly stated, is not intended to designate a particular configuration. Thus a carbon-carbon double bond depicted arbitrarily as E may be Z, E, or a mixture of the two in any proportion. Likewise, all tautomeric forms are also intended to be included.

The graphic representations of racemic, ambiscalemic and scalemic or enantiomerically pure compounds used herein are taken from Maehr J. Chem. Ed. 62, 114-120 (1985): solid and broken wedges are used to denote the absolute configuration of a chiral element; wavy lines and single thin lines indicate disavowal of any stereochemical implication which the bond it represents could generate; solid and broken bold lines are geometric descriptors indicating the relative configuration shown but denoting racemic character; and wedge outlines and dotted or broken lines denote enantiomerically pure compounds of indeterminate absolute configuration.

Terminology related to "protecting", "deprotecting" and "protected" functionalities occurs throughout this application. Such terminology is well understood by persons of skill in the art and is used in the context of processes that involve sequential treatment with a series of reagents. In that context, a protecting group refers to a group, which is used to mask a functionality during a process step in which it would otherwise react, but in which reaction is undesirable. The protecting group prevents reaction at that step, but may be subsequently removed to expose the original functionality. The removal or "deprotection" occurs after the completion of the reaction or reactions in which the functionality would interfere. Thus, when a sequence of reagents is specified, as it is in the processes of the invention, the person of ordinary skill can readily envision those groups that would be suitable as "protecting groups". Suitable groups for that purpose are discussed in standard textbooks in the field of chemistry, such as Protective Groups in Organic Synthesis by T. W. Greene [John Wiley & Sons, New York, 1991], which is incorporated herein by reference.

A comprehensive list of abbreviations utilized by organic chemists appears in the first issue of each volume of the Journal of Organic Chemistry. The list, which is typically presented in a table entitled "Standard List of Abbreviations", is incorporated herein by reference.

In general, the compounds of the present invention may be prepared by the methods illustrated in the general reaction schemes as, for example, described below, or by modifications thereof, using readily available starting materials, reagents and conventional synthesis procedures. In these reactions, it is also possible to make use of variants that are in themselves known, but are not mentioned here. The starting materials, for example in the case of suitably substituted benzimidazole ring compounds, are either commercially available, synthesized as described in the examples or may be obtained by the methods well known to persons of skill in the art.

LTA4H inhibitors have been shown to be effective anti-inflammatory agents in pre-clinical studies. For example, oral administration of LTA4H inhibitor SC57461 to rodents resulted in the inhibition of ionophore-induced LTB4 production in mouse blood ex vivo, and in rat peritoneum in vivo (Kachur et al., 2002, J. Pharm. Exp. Ther. 300(2), 583-587). Furthermore, eight weeks of treatment with the same inhibitor compound significantly improved colitis symptoms in a primate model (Penning, 2001, Curr. Pharm. Des. 7(3): 163-179). The spontaneous colitis that develops in these animals is very similar to human IBD. Therefore persons of skill in the art accept that positive results in LTA4H models are predictive of therapeutic utility in this and other human inflammatory diseases.

The inflammatory response is characterized by pain, increased temperature, redness, swelling, or reduced function, or by a combination of two or more of these symptoms. The terms inflammation, inflammatory diseases or inflammation-mediated diseases or conditions include, but are not limited to, acute inflammation, allergic inflammation, and chronic inflammation.

Autoimmune diseases are associated with chronic inflammation. There are about 75 different autoimmune disorders known that may be classified into two types, organ-specific (directed mainly at one organ) and non-organ-specific (affecting multiple organs).

Examples of organ-specific autoimmune disorders are insulin-dependent diabetes (Type I) which affects the pancreas, Hashimoto's thyroiditis and Graves' disease which affect the thyroid gland, pernicious anemia which affects the stomach, Cushing's disease and Addison's disease which affect the adrenal glands, chronic active hepatitis which affects the liver; polycystic ovary syndrome (PCOS), celiac disease, psoriasis, inflammatory bowel disease (IBD) and ankylosing spondylitis.

Examples of non-organ-specific autoimmune disorders are rheumatoid arthritis, multiple sclerosis, systemic lupus and myasthenia gravis.

Furthermore, the compounds, compositions and methods of the present invention are useful in treating cancer. Leukotriene synthesis has been shown to be associated with different types of cancer including esophageal cancer, brain cancer, pancreatic cancer, colon cancer.

The terms "methods of treating or preventing" mean amelioration, prevention or relief from the symptoms and/or effects associated with lipid disorders. The term "preventing" as used herein refers to administering a medicament beforehand to forestall or obtund an acute episode. The person of ordinary skill in the medical art (to which the present method claims are directed) recognizes that the term "prevent" is not an absolute term. In the medical art it is understood to refer to the prophylactic administration of a drug to substantially diminish the likelihood or seriousness of a condition, and this is the sense intended in applicants' claims. As used herein, reference to "treatment" of a patient is intended to include prophylaxis. Throughout this application, various references are referred to. The disclosures of these publications in their entireties are hereby incorporated by reference as if written herein.

The term "mammal" is used in its dictionary sense. Humans are included in the group of mammals, and humans would be the preferred subjects of the methods of While it may be possible for the compounds of formula Ψ to be administered as the raw chemical, it is preferable to present them as a pharmaceutical composition. According to a further aspect, the present invention provides a pharmaceutical composition comprising a compound of formula I, or a pharmaceutically acceptable salt or solvate thereof, together with one or more pharmaceutically carriers thereof and optionally one or more other therapeutic ingredients. The carrier(s) must be "acceptable" in the sense of being compatible with the other ingredients of the formulation and not deleterious to the recipient thereof.

The formulations include those suitable for oral, parenteral (including subcutaneous, intradermal, intramuscular, intravenous and intraarticular), rectal and topical (including dermal, buccal, sublingual and intraocular) administration. The most suitable route may depend upon the condition and disorder of the recipient. The formulations may conveniently be presented in unit dosage form and may be prepared by any of the methods well known in the art of pharmacy. All methods include the step of bringing into association a compound of formula Ψ or a pharmaceutically acceptable salt or solvate thereof ("active ingredient") with the carrier, which constitutes one or more accessory ingredients. In general, the formulations are prepared by uniformly and intimately bringing into association the active ingredient with liquid carriers or finely divided solid carriers or both and then, if necessary, shaping the product into the desired formulation.

Formulations of the present invention suitable for oral administration may be presented as discrete units such as capsules, cachets or tablets each containing a predetermined amount of the active ingredient; as a powder (including micronized and nanoparticulate powders) or granules; as a solution or a suspension in an aqueous liquid or a non-aqueous liquid; or as an oil-in-water liquid emulsion or a water-in-oil liquid emulsion. The active ingredient may also be presented as a bolus, electuary or paste.

A tablet may be made by compression or molding, optionally with one or more accessory ingredients. Compressed tablets may be prepared by compressing in a suitable machine the active ingredient in a free-flowing form such as a powder or granules, optionally mixed with a binder, lubricant, inert diluent, lubricating, surface active or dispersing agent. Molded tablets may be made by molding in a suitable machine a mixture of the powdered compound moistened with an inert liquid diluent. The tablets may optionally be coated or scored and may be formulated so as to provide sustained, delayed or controlled release of the active ingredient therein.

The pharmaceutical compositions may include a "pharmaceutically acceptable inert carrier", and this expression is intended to include one or more inert excipients, which include starches, polyols, granulating agents, microcrystalline cellulose, diluents, lubricants, binders, disintegrating agents, and the like. If desired, tablet dosages of the disclosed compositions may be coated by standard aqueous or non-aqueous techniques, "Pharmaceutically acceptable carrier" also encompasses controlled release means.

Compositions of the present invention may also optionally include other therapeutic ingredients, anti-caking agents, preservatives, sweetening agents, colorants, flavors, desiccants, plasticizers, dyes, and the like. Any such optional ingredient must, of course, be compatible with the compound of the invention to insure the stability of the formulation. The dose range for adult humans is generally from 0.1 μg to 10 g/day orally. Tablets or other forms of presentation provided in discrete units may conveniently contain an amount of compound of the invention which is effective at such dosage or as a multiple of the same, for instance, units containing 0.1 mg to 500 mg, usually around 5 mg to 200 mg. The precise amount of compound administered to a patient will be the responsibility of the attendant physician. However, the dose employed will depend on a number of factors, including the age and sex of the patient, the precise disorder being treated, and its severity. The frequency of administration will depend on the pharmacodynamics of the individual compound and the formulation of the dosage form, which may be optimized by methods well known in the art (e.g. controlled or extended release tablets, enteric coating etc.).

Combination therapy can be achieved by administering two or more agents, each of which is formulated and administered separately, or by administering two or more agents in a single formulation. Other combinations are also encompassed by combination therapy. For example, two agents can be formulated together and administered in conjunction with a separate formulation containing a third agent. While the two or more agents in the combination therapy can be administered simultaneously, they need not be. For example, administration of a first agent (or combination of agents) can precede administration of a second agent (or combination of agents) by minutes, hours, days, or weeks. Thus, the two or more agents can be administered within minutes of each other or within any number of hours of each other or within any number or days or weeks of each other. In some cases even longer intervals are possible.

While in many cases it is desirable that the two or more agents used in a combination therapy be present in within the patient's body at the same time, this need not be so. Combination therapy can also include two or more administrations of one or more of the agents used in the combination. For example, if agent X and agent Y are used in a combination, one could administer them sequentially in any combination one or more times, e.g., in the order X—Y—X, X—X—Y, Y—X—Y, Y—Y—X, X—X—Y—Y, etc.

As LTA4H inhibitors, the compounds of formula Ψ have utility in treating and preventing inter alia inflammation. The compounds and compositions can be used advantageously in combination with other agents useful in treating and preventing inflammatory conditions and for treating and preventing atherosclerosis, thrombosis, stroke, acute coronary syndrome, stable angina, peripheral vascular disease, critical leg ischemia, intermittent claudication, abdominal aortic aneurysm and myocardial infarction.

In general, the compounds of the present invention may be prepared by the methods illustrated in the general reaction schemes as, for example, described below, or by modifications thereof, using readily available starting materials, reagents and conventional synthesis procedures. The following specific non-limiting examples are illustrative of the invention.

Scheme I

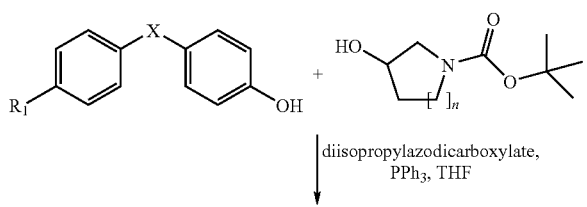

diisopropylazodicarboxylate, PPh$_3$, THF

-continued

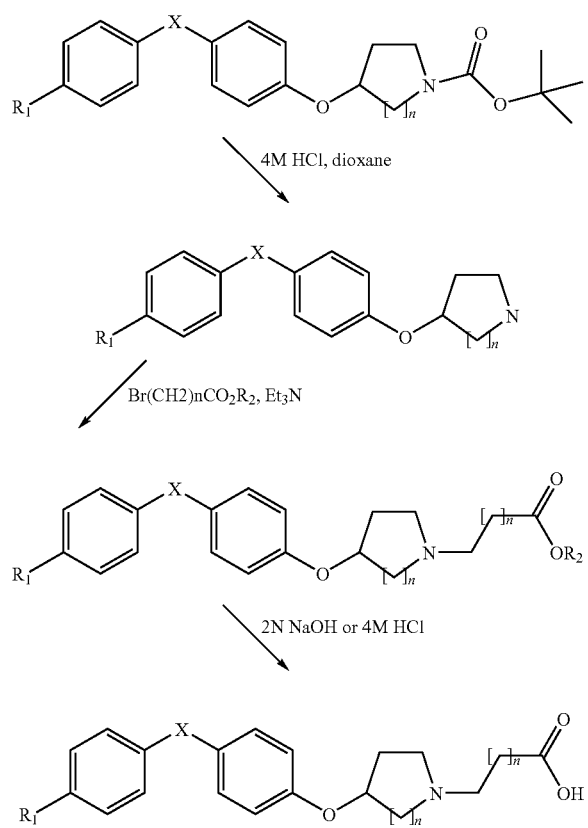

R₁ = H, CF₃, Ph
X = C, O
R₂ = H, Me
n = 0, 1

EXAMPLE 1

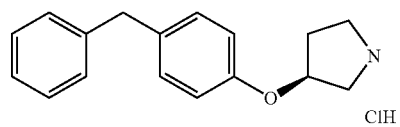

(S) 3-(4-Benzyl-phenoxy)-pyrrolidine hydrochloride salt: To a solution of (R)-3-hydroxy-pyrrolidine carboxylic acid-t-butyl ester (187 mg, 1.0 mmol) in anhydrous THF (1 mL) was added 4-hydroxydiphenyl methane (240 mg, 1.3 mmol) in THF (1 mL) and triphenyl phosphine (315 mg, 1.2 mmol) in THF (1 mL). The resulting mixture was cooled to 0° C. using ice-water bath and purged with nitrogen. Diisopropyl azodicarboxylate (242 mg, 1.2 mmol) was dissolved in 2 mL of THF and added to above solution dropwise over a period of 15 min under nitrogen. Reaction then was heated at 70° C. for 16 h. THF was removed in vacuo and crude mixture was purified by silica gel flash chromatography (10% EtOAc/Hexane) to obtain the product. To a solution of the product in dioxane (1 mL) was added 4M HCl in dioxane (3 mL) at rt and the resulting mixture was stirred for 30 min at that temperature. The solvent was removed in vacuo to obtain thick oil. The oil was triturated with ether to obtain a white solid (143 mg, 49%): MS; m/z 254.5 (M+H); $^1$H NMR (400 MHz, DMSO-$d_6$); δ 2.09-2.18 (m, 2H), 3.23-3.31 (m, 4H), 3.40-344 (m, 1H), 3.87 (s, 2H), 5.07 (m, 1H), 6.88 (dd, 2H, J1=6.4 Hz, J2=2 Hz), 7.16-7.22 (m, 5H), 7.26-7.29 (m, 2H), 9.30 (s, 2H);

Scheme II

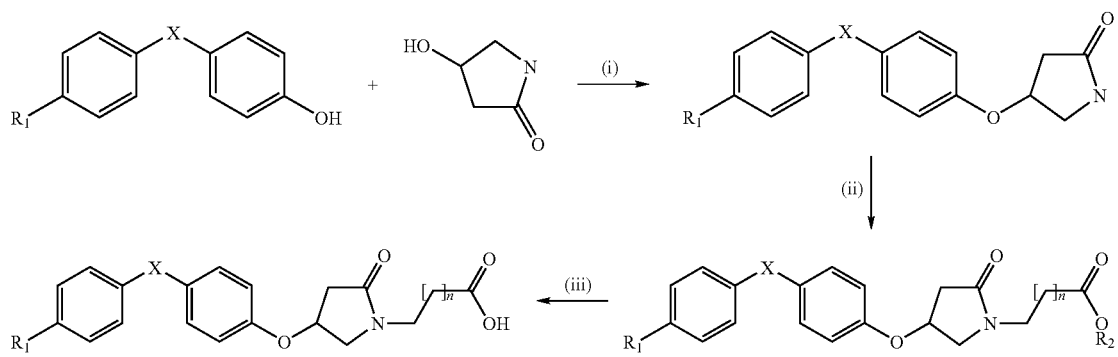

R₁ = H, CF₃, Ph
X = C, O
R₂ = H, Me
n = 0, 1
Scheme I:
(i) diisopropylazodicarboxylate, PPh₃, THF;
(ii) Br(CH₂)nCO₂R₂, Et₃N,
(iii) 2N NaOH or 4M HCl HPLC (UV); 98%. Elemental analysis: Calc C 70.46 H 6.96 N 4.83. Found C 70.64 H 7.06 N 4.90

EXAMPLE 2

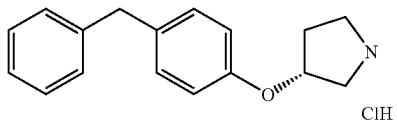

(R) 3-(4-Benzyl-phenoxy)-pyrrolidine hydrochloride salt: To a solution of (S)(+)-1BOC-3-hydroxy pyrrolidine (936 mg, 5.0 mmol) in anhydrous THF (5 mL) was added 4-hydroxydiphenyl methane (1197 mg, 6.5 mmol) in THF (5 mL) and triphenyl phosphine (1574 mg, 6 mmol) in THF (5 mL). The resulting mixture was cooled to 0° C. using ice-water bath and purged with nitrogen. Diisopropyl azodicarboxylate (1213 mg, 6 mmol) was dissolved in 5 mL of THF and added to above solution drop wise over period of 30 min under nitrogen. Reaction then was heated at rt for 3 hrs and 70° C. for 16 h. THF was removed in vacuo and crude mixture was purified by silica gel flash chromatography (10% EtOAc/Hexane) to obtain the product. To a solution of the product in dioxane (4 mL) was added 4M HCl in dioxane (10 mL) at rt and the resulting mixture was stirred for 3 h at that temperature. The solvent was removed in vacuo and residue was triturated with ether to obtain a white crystalline solid (788 mg, 63%): MS; m/z 254.4 (M+H); $^1$H NMR (400 MHz, DMSO-$d_6$); δ 2.09-2.17 (m, 2H), 3.19-3.33 (m, 4H), 3.40-3.44 (m, 1H), 3.87 (s, 2H), 5.07 (m, 1H), 6.88 (dd, 2H, J1=6.4 Hz, J2=2 Hz), 7.15-7.22 (m, 1H), 7.26-7.29 (m, 2H), 9.44 (s, 2H); HPLC (UV); 99.1%.

EXAMPLE 3

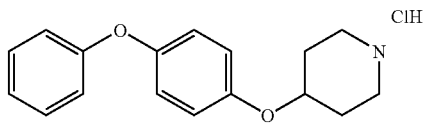

4-(4-Phenoxy-phenoxy)-piperidine hydrochloride salt: To a solution of t-butyl-4-hydroxy-1-piperidine carboxylate (1.0 g, 5.0 mmol) in anhydrous THF (5 mL) was added 4-phenoxyphenol (1.21 g, 6.5 mmol) in THF (5 mL) and triphenyl phosphine (1.57 g, 6 mmol) in THF (5 mL). The resulting mixture was cooled to 0° C. using ice-water bath and purged with nitrogen. Diisopropyl azodicarboxylate (1.21 g, 6 mmol) was dissolved in 5 mL of THF and added to above solution drop wise over period of 20 min under nitrogen. Reaction then was heated at rt for 3 h and 70° C. for 48 h. THF was removed in vacuo and crude mixture was purified by silica gel flash chromatography (10% EtOAc/Hexane) to obtain the product. To a solution of the product in dioxane (4 mL) was added 4M HCl in dioxane (10 mL) at rt and the resulting mixture was stirred for 3 h at that temperature. The solvent was removed in vacuo and residue was triturated with ether to obtain a white crystalline solid (918 mg, 68%): MS; m/z 270.5 (M+H); $^1$H NMR (400 MHz, DMSO-$d_6$); δ 1.81-1.87 (m, 2H), 2.07-2.12 (m, 2H), 3.02-3.08 (m, 2H), 3.19-3.25 (m, 2H), 3.56 (s, 1H), 4.57-4.61 (m, 1H), 6.92-7.10 (m, 7H), 7.33-7.37 (m, 2H), 8.91 (s, 2H); HPLC (UV); 96%. Elemental analysis. Calc C 66.77 H 6.59 N 4.58. Found C 65.82 H 6.70 N 4.77.

EXAMPLE 4

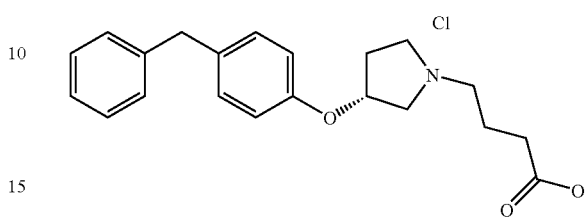

Step 1

4-[(R)-3-(4-Benzyl-phenoxy)-pyrrolidin-1-yl]-butyric acid methyl ester: To a solution of (R)-3-(4-Benzyl-phenoxy)-pyrrolidine (126 mg, 0.5 mmol) in anhydrous CH2Cl2 (0.5 mL) was added methyl-4-bromobutyrate (99 mg, 0.55 mmol) in CH2Cl2 (0.5 mL) and triethylamine (101 mg, 1.0 mmol. The resulting mixture was purged with nitrogen and stirred at rt for 16 h. CH2Cl2 was removed in vacuo and crude mixture was partioned between EtOAc and water. EtOAc layer was removed, washed with brine, dried over anhydrous MgSO4 and concentrated. The crude mixture was purified by silica gel flash chromatography (40% EtOA /Hexane) to obtain the product as yellow solid (71 mg, 40%): MS; m/z 354.5 (M+H); $^1$H NMR (400 MHz, DMSO-$d_6$); δ 1.65-1.72 (m, 2H), 2.18-2.39 (m, 4H), 2.54-2.63 (m, 5H), 2.78-2.82 (m, 1H), 3.57 (s, 3H), 3.85 (s, 2H), 5.78 (m, 1H), 6.78 (d, 2H, J=8.8 Hz), 7.11 (d, 2H, J=8.4Hz), 7.16-7.29 (m, 5H); HPLC (ELSD); 99%.

Step 2

4-[(R)-3-(4-Benzyl-phenoxy)-pyrrolidin-1-yl]-butyric acid hydrochloride salt: To a solution of the product (65 mg, 0.184 mmol) from step 1 in 4:1 mixture of MeOH/water (1 mL) was added 2M solution of NaOH (110 uL, 0.221 mmol). Reaction mixture was heated at 50° C. for 16 h. Solvent was removed in vacuo, residue was dissolved in water and pH was adjusted to 2 with 1M HCl solution. Then product was extracted with EtOAc, washed with water, brine, dried over anhydrous MgSO4 and concentrated to give the title compound (43 mg, 70%): MS; m/z 340.5 (M+H); $^1$H NMR (400 MHz, DMSO-$d_6$); δ 1.85-1.91 (m, 2H), 2.08 (br, 1H), 2.33 (m, 3H), 3.14-3.18 (m, 6H), 3.88 (s, 2H), 5.07 (s, 1H), 6.87-6.89 (m, 2H), 7.15-7.22 (m, 5H), 7.26-7.29 (m, 2H); HPLC (ELSD); 99%. Elemental analysis: Calc C 67.10 H 6.97 N 3.73. Found C 66.99 H 7.03 N 3.79.

EXAMPLE 5

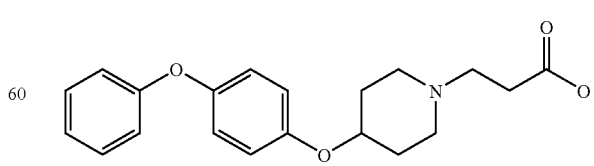

Step 1

3-[4-(4-Phenoxy-phenoxy)-piperidin-1-yl]-propionic acid methyl ester: To a solution of 4-(4-Phenoxy-phenoxy)-piperidine (152 mg, 0.5 mmol) in anhydrous CH2Cl2 (0.5 mL) was added methyl-3-bromopropionate (91 mg, 0.55 mmol) in CH2Cl2 (0.5 mL) and triethylamine (101 mg, 1.0 mmol). The resulting mixture was purged with nitrogen and stirred at rt for 48 h. CH2Cl2 was removed in vacuo and crude mixture was partioned between EtOAc and water. EtOAc layer was removed, washed with saturated NaHCO3, dried over anhydrous MgSO4 and concentrated. The crude mixture was purified by silica gel flash chromatography (50% EtOAc/Hexane) to obtain the product (146 mg, 82%): MS; m/z 356.5 (M+H); $^1$H NMR (400 MHz, DMSO-$d_6$); δ 1.56-1.60 (m, 2H), 1.89-1.92 (m, 2H), 2.19-2.49 (m, 2H), 2.46-2.49 (m, 2H), 2.58 (t, 2H, J=6.8Hz), 2.60-2.69 (m, 2H), 3.59 (s, 3H), 4.28-4.30 (m, 1H), 6.91-6.96 (m, 6H), 7.04-7.08 (m, 1H), 7.32-7.36 (m, 2H); HPLC (UV); 94.7%.

Step 2

3-[4-(4-Phenoxy-phenoxy)-piperidin-1-yl]-propionic acid: To a solution of the product (143 mg, 0.4 mmol) from step 1 in 4:1 mixture of MeOH/water (2 mL) was added 2M solution of NaOH (241 uL, 0.48 mmol). Reaction mixture was heated at 50° C. for 16 h. Solvent was removed in vacuo, residue was washed with water, dissolved in MeOH and filtered. Filtrate was concentrated to give the product as white solid (155 mg, 100%): MS; m/z 342.5 (M+H); $^1$H NMR (400 MHz, DMSO-$d_6$); δ 1.99 (br, 2H), 2.17-2.21 (m, 2H), 2.84-2.88 (m, 2H), 3.25-3.32 (m, 7H), 6.92-7.10 (m, 7H), 7.33-7.37 (m, 2H); HPLC (UV); 93%.

EXAMPLE 6

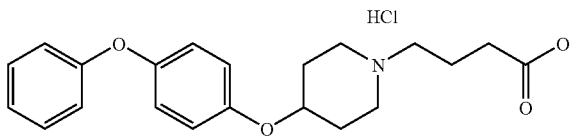

Step 1

4-[4-(4-Phenoxy-phenoxy)-piperidin-1-yl]-butyric acid methyl ester: To a solution of 4-(4-Phenoxy-phenoxy)-piperidine (152 mg, 0.5 mmol) in anhydrous CH2Cl2 (0.5 mL) was added methyl-3-bromopropionate (99 mg, 0.55 mmol) in CH2Cl2 (0.5 mL) and triethylamine (101 mg, 1.0 mmol). The resulting mixture was purged with nitrogen and stirred at if for 48 h. CH2Cl2 was removed in vacuo and crude mixture was partioned between EtOAc and water. EtOAc layer was removed, washed with brine, dried over anhydrous MgSO4 and concentrated. The crude mixture was purified by silica gel flash chromatography (40-70% EtOAc/Hexane) to obtain the product as yellow oil (125 mg, 68%): $^1$H NMR (400 MHz, DMSO-$d_6$); δ 1.54-1.69 (m, 4H), 1.89-1.92 (m, 2H), 2.14-2.18 (m, 2H), 2.26-2.33 (m, 4H), 2.64-2.67 (m, 2H), 3.58 (s, 3H), 4.27-4.31 (m, 1H), 6.91-6.96 (m, 6H), 7.04-7.08 (m, 1H), 7.32-7.36 (m, 2H).

Step 2

4-[4-(4-Phenoxy-phenoxy)-piperidin-1-yl]-butyric acid hydrochloride salt: To a solution of the product (120 mg, 0.32 mmol) from step 1 in 4:1 mixture of MeOH/water (2 mL) was added 2M solution of NaOH (195 uL, 0.39 mmol). Reaction mixture was heated at 50° C. for 16 h. Solvent was removed in vacuo, residue was dissolved in water and pH was adjusted to 2 with 1 M HCl solution. Then product was extracted with EtOAc, washed with water, brine, dried over anhydrous MgSO4 and concentrated to give the title compound as white solid (65 mg, 58%): MS; m/z 356.6 (M+H); $^1$H NMR (400 MHz, DMSO-$d_6$); δ 1.87-1.95 (m, 5H), 2.15 (br, 2H), 2.34 (t, 2H, J=7.2 Hz), 3.06-3.1 (m, 4H), 3.26-3.36 (m, 2H), 6.92-7.01 (m, 7H), 7.33-7.36 (m, 2H); HPLC (ELSD); 99%.

EXAMPLE 7

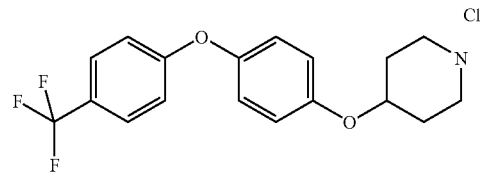

4-[4-(4-Trifluoromethyl-phenoxy)-phenoxy]-piperidine hydrochloride salt: To a solution of t-butyl-4-hydroxy-1-piperidine carboxylate (1.0 g, 5.0 mmol) in anhydrous THF (5 mL) was added 4-[(4-trifluoromethyl)phenoxy]phenol (1.65 g, 6.5 mmol) in THF (5 mL) and triphenyl phosphine (1.57 g, 6 mmol) in THF (5mL). The resulting mixture was cooled to 0° C. using ice-water bath and purged with nitrogen. Diisopropyl azodicarboxylate (1.21 g, 6 mmol) was dissolved in 5 mL of THF and added to above solution drop wise over a period of 30 min under nitrogen. Reaction then was stirred at 0° C. for 0.5 h heated at 70° C. for 16 h. THF was removed in vacuo and crude mixture was purified by silica gel flash chromatography (10% EtOAc/Hexane) to obtain the product. To a solution of the product in dioxane (4 mL) was added 4M HCl in dioxane (10 mL) at rt and the resulting mixture was stirred for 2 h at that temperature. The solvent was removed in vacuo and residue was triturated with ether to obtain a white solid (1.21 g, 65%): MS; m/z 338.4 (M+H), $^1$H NMR (400 MHz, DMSO-$d_6$); δ 1.83-1.90 (m, 2H), 2.09-2.14 (m, 2H), 3.03-3.09 (m, 2H), 3.20-3.26 (m, 2H), 3.32 (s, 1H), 4.62-4.66 (m, 1H), 7.06-7.10 (m, 7H), 7.70 (d, 2H, J=8.8 Hz), 9.08 (s, 2H); HPLC (UV); 97%.

EXAMPLE 8

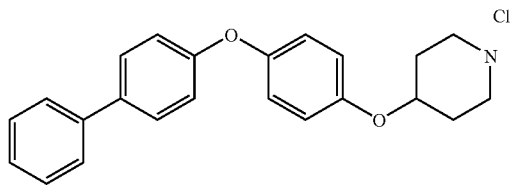

Step 1

4-(4-Methoxy-phenoxy)-biphenyl: A mixture of 4-bromobiphenyl (1.16 g, 5 mmol), 4-methoxyphenol (413 mg, 3.33 mmol), Cs2CO3 (2.17 g, 6.66 mmol) in anhydrous dioxane (10 mL) was purged with nitrogen for 10 min. Then copper (I) iodide (18 mg, .096 mmol) and N,N-dimethylglycine.HCl (41 mg, 0.29 mmol) were added. Reaction was stirred at 90° C. over night. Reaction mixture was cooled and poured over 1:1 mixture of EtOAc/water. Organic layer was separated, washed with water, brine, dried over anhydrous MgSO4 and concentrated to give the crude product. It was used in next step without purification (1.26 g, 91%).

Step 2

4-(Biphenyl-4-yloxy)-phenol:4-(4-Methoxy-phenoxy)-biphenyl (1.0 g, 3.6 mmol) in anhydrous CH2Cl2 (10 mL) was cooled to −78° C. and 1M boron tribromide (10.8 mL, 10.8 mmol) in CH2Cl2 was added dropwise over period of 20 min under nitrogen. The resulting mixture was stirred at −78° C. for 2 h and at rt for 1 h. Then it was cooled to 0° C. and poured slowly over 1:1 mixture of CH2Cl2/water. CH2Cl2 layer was separated, washed with water, brine, dried over anhydrous MgSO4 and concentrated. The crude product was purified using silica gel flash chromatography (20% EtOAc/Hexane) to obtain the product as yellow solid (265 mg, 28%): MS; m/z 260.9 (M−H); $^1$H NMR (400 MHz, DMSO-$d_6$); δ 6.79-6.82 (m, 1H), 6.91-6.98 (m, 2H), 7.30-7.49 (m, 4H), 7.60-7.68 (m, 6H), 8.36 (s, 1H).

Step 3

4-[4-(Biphenyl-4-yloxy)-phenoxy]-piperidine hydrochloride salt; To a solution of t-butyl-4-hydroxy-1-piperidine carboxylate (201 mg, 1 mmol) in anhydrous THF (1 mL) was added 4-(biphenyl-4-yloxy)-phenol (262 mg, 1 mmol) in THF (1 mL) and triphenyl phosphine (314 mg, 1.2 mmol) in THF (1 mL). The resulting mixture was cooled to 0° C. using ice-water bath and purged with nitrogen. Diisopropyl azodicarboxylate (242 mg, 1.2 mmol) was dissolved in 2 mL of THF and added to above solution drop wise over a period of 15 min under nitrogen. Reaction then was stirred at 0° C. for 2 h heated at 70° C. for 16 h. THF was removed in vacuo and crude mixture was purified by silica gel flash chromatography (10% EtOAc/Hexane) to obtaim the product. To a solution of the product in dioxane (1 mL) was added 4M HCl in dioxane (5 mL) at rt and the resulting mixture was stirred for 2 h at that temperature. Precipitated white solid was removed by filtration, washed with ether and dried in vacuum (185, 43%): MS; m/z 346.4(M+H); $^1$H NMR (400 MHz, DMSO-$d_6$); δ 1.82-1.88 (m, 2H), 2.08-2.2.13 (m, 2H), 3.03-3.09 (m, 2H), 3.21-3.32 (m, 2H), 4.59-4.62 (m, 1H), 7.00-7.06 (m, 6H), 7.32-7.36 (m, 1H), 7.42-7.47 (m, 2H), 7.61-7.66 (m, 4H), 8.87 (s, 1H); HPLC (UV); 99%.

EXAMPLE 9

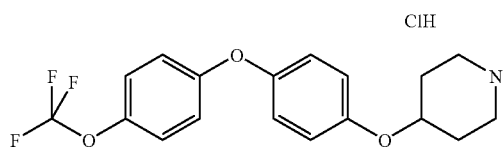

4-[4-(4-Trifluoromethoxy-phenoxy)-phenoxy]-piperidine hydrochloride: To a solution of t-butyl-4-hydroxy-1-piperidinecarboxylate (0.40 g, 1.99 mmol) in anhydrous THF (8 mL) was added 4-(4-Trifluoromethoxy-phenoxy)-phenol (0.58 g, 2.65 mmol) and triphenylphosphine (0.63 g, 2.40 mmol). The resulting mixture was cooled to 0° C. Diisopropylazodicarboxylate (0.47 mL, 2.43 mmol) was added portionwise over a ten minute period. The reaction mixture was warmed to ambient temperature for an hour and then heated to 60° C. for 48 h. The solvent was removed in vacuo. The crude residue was purified by silica gel flash chromatography using hexane/EtOAc (gradient system) to give a yellow oil. To the oil was added 4 M HCl in dioxane (7 mL). The resulting mixture was stirred at ambient temperature 2 h. The solvent was removed under reduced pressure to obtain crude product. The residue was triturated with ether to afford the title compound (98 mg, 14%); $^1$H NMR (400 MHz, DMSO-$d_6$); δ 1.85 (m, 2H), 2.10 (m, 2H), 3.06 (m, 2H), 3.23 (m, 2H), 4.61 (m, 1H), 7.02 (d, J=8.8 Hz, 2H), 7.06 (s, 3H), 7.35 (d, J=8.8 Hz, 2H), 8.92 (br s, 2H); MS (m/z) 354.4 (M+1); LC (97.5%).

EXAMPLE 10

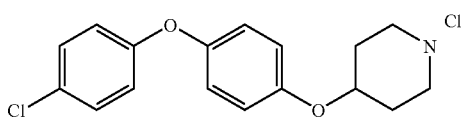

Step 1

4-[4-(4-Chloro-phenoxy)-phenoxy]-piperidine: To a solution of t-butyl-4-hydroxy-1-piperidinecarboxylate (0.40 g, 1.99 mmol) in anhydrous THF (8 mL) was added 4-(4-chlorophenoxy)-phenol (0.58 g, 2.61 mmol) and triphenylphosphine (0.63 g, 2.40 mmol). The resulting mixture was cooled to 0° C. Diisopropylazodicarboxylate (0.47 mL, 2.43 mmol) was added portionwise over a ten minute period. The reaction mixture was warmed to ambient temperature for an hour and then heated to 47° C. for 64 h. The solvent was removed in vacuo. The crude residue was purified by silica gel flash chromatography using hexane/EtOAc (gradient system) to give the title compound (0.93 g, 100%) as a yellow oil.

Step 2

4-[4-(4-Chloro-phenoxy)-phenoxy]-piperidine hydrochloride: To the product from step 1 (0.88 g, 2.17 mmol) was added 4 M HCl in dioxane (10 mL). The resulting mixture was stirred at ambient temperature for 2 hours. The solvent was removed under reduced pressure. The residue was triturated with ether to afford the title compound (0.34 g, 47%) as a white solid; $^1$H NMR (400 MHz, DMSO-$d_6$); δ 1.83 (m, 2H), 2.09 (m, 2H), 3.06 (m, 2H), 3.23 (m, 2H), 4.60 (m, 1H), 6.94 (d, J=9.2 Hz, 2H), 7.01-7.06 (m, 4H), 7.40 (d, J=9.2 Hz, 2H), 8.81 (br s, 2H); MS (m/z) 304.4 (M+1); LC (100%).

EXAMPLE 11

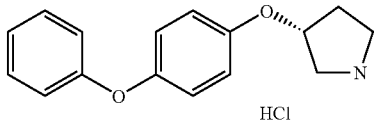

(R)-3-(4-Phenoxy-phenoxy)-pyrrolidine hydrochloride: N-t-butylcarbonyl-(R)-(−)-3-pyrrolidinol (1 g, 5.34 mmol) was taken into anhydrous tetrahydrofuran (2 mL) in a nitrogen flushed 20 mL vial. 4-phenoxyphenol (1.29 g, 6.94 mmol) was added to the mixture followed by triphenylphosphine (1.86 g, 6.41 mmol). The reaction was cooled to 0° C. and a solution of diisopropyl azodicarboxylate (1.3 g, 6.41 mmol) in anhydrous tetrahydrofuran (2 mL) was slowly added to the reaction over 5 min. The mixture was then allowed to warm to room temperature overnight. The reaction was concentrated to dryness under vacuum and the residue was purified by flash silica chromatography (20:1 silica packing ratio, eluted with 1% methanol in dichloromethane). The enriched product was then taken into 4N HCl in dioxane, and stirred at room temperature overnight. The mixture was then concentrated to dryness and triturated with diethyl ether to provide the title product (1.24 g, 80%); LCMS; m/z 256 (M+1 of free amine). ¹H NMR (400 MHz, DMSO); δ 2.13-2.17 (m, 2H), 3.25-3.47 (m, 4H), 5.10 (s, 1H), 6.93-6.95 (m, 2H), 7.02 (s, 4H), 7.09-7.11 (m, 1H), 7.34-7.38 (m, 2H), 9.54 (s, 2H).

EXAMPLE 12

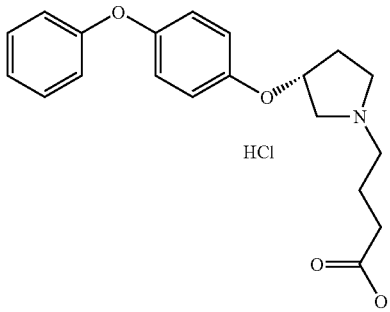

Step 1

4-[(R)-3-(4-Phenoxy-phenoxy)-pyrrolidin-1-yl]-butyric acid methyl ester: (R)-3-(4-Phenoxy-phenoxy)-pyrrolidine (1.24 g, 4.25 mmol) was taken into anhydrous DMF (10 mL) in a nitrogen flushed 100 mL, 1-neck round bottom flask. Methyl-4-bromobutyrate (846 mg, 4.68 mmol) was added to the mixture followed by potassium carbonate (1.18 g, 8.5 mmol). The reaction was heated at 60° C. for 24 h. The mixture was then cooled to room temperature and partitioned between ethyl acetate and water. The water layer was washed with ethyl acetate (3×). The combined ethyl acetate layers were then washed with brine, dried over anhydrous sodium sulfate, filtered, and concentrated to dryness. The resulting residue was then purified by silica gel flash chromatography (20:1 silica ratio, eluted with 1:1 ethyl acetate and hexane) to obtain the title product (894.4 mg, 59%) LCMS; m/z 356 (M+1); ¹H NMR (400 MHz, DMSO) δ 1.65-1.78 (m, 3H), 2.21-2.26 (m, 1H), 2.32-2.35 (m, 2H), 2.37-2.42 (m, 3H), 2.58-2.61 (m, 1H), 2.63-2.69 (m, 1H), 2.80-2.84 (m, 1H), 3.58 (s, 3H), 4.80 (s, 1H), 6.89-6.98 (m, 6H), 7.07-7.09 (m, 1H), 7.32-7.36 (m, 2H).

Step 2

4-[(R)-3-(4-Phenoxy-phenoxy)-pyrrolidin-1-yl]-butyric acid hydrogen chloride: The product from step 1 (200 mg, 0.56 mmol), was taken into 1.029N NaOH (aq) (1.0933 mL, 1.125 mmol), and methanol (3 mL). The reaction was heated to 60° C. and run for 24 h. The mixture was concentrated to dryness and taken into 1N HCl in dioxane (1.125 mL, 0.1.125 mmol), and was left to react for 24 h at room temperature. The mixture was concentrated to dryness and taken into dichloromethane. The solution was filtered to remove salts, and then concentrated to dryness. The residue was then taken into an excess of 1N HCl in dioxane and left to react for 24 h. at room temperature. The mixture was then concentrated to dryness to yield the title product (123.5 mg, 0.327 mmol, 58% yield); LC/MS, m/z 343 (m+2 of free amine); ¹H NMR (400 MHz, DMSO) δ 1.89-1.93 (m, 2H), 2.14 (s, 1H), 2.33-2.49 (m, 3H), 3.17-3.21 (m, 3H), 3.57 (s, 2H), 5.10 (s, 1H), 6.92-6.96 (m, 2H), 7.02 (s, 4H), 7.07-7.11 (m, 1H), 7.34-7.38 (m, 2H).

EXAMPLE 13

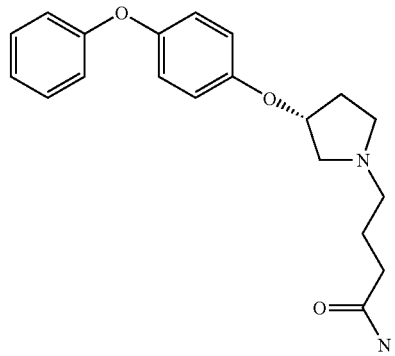

4-[(R)-3-(4-Phenoxy-phenoxy)-pyrrolidin-1-yl]-butyramide: 4-[(R)-3-(4-Phenoxy-phenoxy)-pyrrolidin-1-yl]-butyric acid methyl ester (200 mg, 0.563 mmol) was taken into 7N Ammonia in methanol solution (5 mL) in a pressure tube. The tube was sealed and heated to 100° C. with stirring and left to react for 48 h. The reaction was concentrated to dryness, and purified by flash silica chromatography (20:1 silica ratio, eluted with a gradient of 10% methanol in dichloromethane to 15% methanol in dichloromethane) to provide the title product (141 mg, 74%); LCMS; m/z 341 (M+1); ¹H NMR (400 MHz, DMSO) δ 1.62-1.68 (m, 2H), 1.75-1.78 (m, 1H), 2.06-2.10 (m, 2H), 2.22-2.25 (m, 1H), 2.35-2.43 (m, 3H), 2.59-2.68 (m, 2H), 2.80-2.84 (m, 1H), 4.80-4.83 (m, 1H), 6.69 (s, 1H), 6.89-6.93 (m, 4H), 6.94-6.98 (m, 2H), 7.05-7.09 (m, 1H), 7.24 (s, 1H), 7.32-7.36 (m, 2H).

EXAMPLE 14

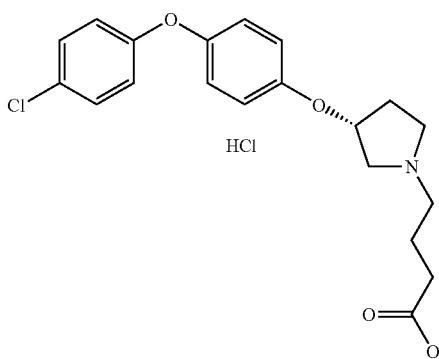

Step 1

(R)-3-(4-Iodo-phenoxy)-pyrrolidine-1-carboxylic acid tert-butyl ester: N-tert-butyl-butoxy carbonyl-(R)-(−)-3-pyrrolidinol (3 g, 16 mmol), 4-iodophenol (4.58 g, 21 mmol), and triphenyl phosphine (5.04 g, 19 mmol), were taken into anhydrous tetrahydrofuran (10 mL) in a nitrogen flushed 200 mL round bottom flask. The reaction was cooled to 0° C. and diisopropyl diazodicarboxylate (1.044 mL, 19 mmol) taken into anhydrous tetrahydrofuran (10 mL) was added to the reaction dropwise over 10 minutes. The reaction was run at 0°

C. for 30 minutes and then allowed to warm to room temperature over 12 h. The reaction was then heated to 70° C. and left to react for 12 h. The mixture was concentrated to dryness, and the compound was purified by flash column chromatography (40:1 silica ratio, eluted with a gradient of dichlormethane to 10% methanol in dichloromethane) to obtain the title product (5.18 g, 83%);LCMS; m/z 390 (M+1) 95% pure. $^1$H NMR (400 MHz, DMSO); δ 1.40 (s, 9H), 2.01-2.03 (m, 2H), 3.03-3.42 (m, 3H), 3.43-3.54 (m, 1H), 4.98 (s, 1H), 6.80 (d, 2H, J=8.8,), 7.60 (d, 2H, J=8.8,).

Step 2

(R)-3-[4-(4-Chloro-phenoxy)-phenoxy]-pyrrolidine-1-carboxylic acid tert-butyl ester: 4-chlorophenol (495 mg, 3.85 mmol), the product from step 1 (1 g, 2.57 mmol), cesium carbonate (1.67 g, 5.14 mmol), copper iodide (51 mg, 0.27 mmol), and N,N-dimethylglycine HCl (35 mg, 0.249 mmol), were taken into anhydrous dioxane (12 mL) in a nitrogen flushed 20 mL vial. The reaction was heated to 90° C. for 24 h. The mixture was concentrated to dryness, and the resulting oil was partitioned between water and ethyl acetate. The aqueous layer was washed with ethyl acetate 3×. The combined organic layers were washed with brine, dried over sodium sulfate and concentrated to dryness. The compound was purified by flash column chromatography (20:1 silica ratio, eluted with 20% ethyl acetate in hexane) to obtain the title product (1 g, ~90%).;LCMS; m/z 390 (M) 88% pure; $^1$H NMR (400 MHz, DMSO); δ 1.41 (s, 9H), 2.00-2.20 (m, 2H), 3.32-3.60 (m, 4H), 4.98 (s, 1H), 6.76 (d, 2H, J=8.8,), 6.94-7.03 (m, 4H), 7.19 (d, 2H, J=8.8,), 9.70 (s, 1H).

Step 3

(R)-3-[4-(4-Chloro-phenoxy)-phenoxy]-pyrrolidine: (R)-3-[4-(4-Chloro-phenoxy)-phenoxy]-pyrrolidine-1-carboxylic acid tert-butyl ester (1 g, 2.56 mmol) was taken into 4N HCl in dioxane (10 mL), and the reaction was run at room temperature for 24 h. The mixture was concentrated to dryness, and the resulting oil was triturated with diethyl ether to obtain the title product (344 mg, 41%); LCMS, m/z 290 (M+1, free amine) 81% pure; $^1$H NMR (400 MHz, DMSO); δ 2.13-2.16 (m, 2H), 3.24-3.33 (m, 4H), 5.11 (s, 1H), 6.95 (d, J=8.8, 2H), 7.04 (s, 4H), 7.40 (d, J=8.8, 2H), 9.66 (s, 2H).

Step 4

4-{(R)-3-[4-(4-Chloro-phenoxy)-phenoxy]-pyrrolidin-1-yl}-butyric acid methyl ester: (R)-3-[4-(4-Chloro-phenoxy)-phenoxy]-pyrrolidine (344 mg, 1.05 mmol) was taken into anhydrous dimethylformamide (5 mL), and methyl-4-bromobutyrate (209 mg, 1.16 mmol), potassium carbonate (290 mg, 2.1 mmol) was added. The reaction was sealed and heated to 60° C. and left to react for 24 h. The mixture was then partitioned between ethyl acetate and water. The aqueous layer was washed with ethyl acetate 3×. The combined organic layers were washed with brine, dried over sodium sulfate and concentrated to dryness. The residue was purified by flash column chromatography (50:1 packing ration, eluted with 5% methanol in dichloromethane) to obtain the title product (86.8 mg, 21%); LCMS; m/z 390 (M) 71% pure; $^1$H NMR (400 MHz, DMSO); δ 1.66-1.80 (m, 3H), 2.22-2.26 (m, 1H), 2.31-2.35 (m, 2H), 2.37-2.41 (m, 3H), 2.58-2.67 (m, 2H), 2.81-2.84 (m, 1H), 3.58 (s, 3H), 4.80-4.83 (m, 1H), 6.91-6.95 (m, 4H), 6.98-7.00 (m, 2H), 7.37-7.39 (m, 2H).

Step 5

4-{(R)-3-[4-(4-Chloro-phenoxy)-phenoxy]-pyrrolidin-1-yl}-butyric acid HCl: 4-{(R)-3-[4-(4-Chloro-phenoxy)-phenoxy]-pyrrolidin-1-yl}-butyric acid methyl ester (86.8 mg, 0.222 mmol) was taken into 1.029N NaOH solution in water (0.433 mL, 0.445 mmol), and methanol (2 mL). The reaction was sealed and heated to 60° C. and left to react for 24 h. The reaction was concentrated to dryness and taken into 4N HCl in dioxane (0.111 ml, 0.445 mmol) and dichloromethane (1 mL). The reaction was stirred for 15 minutes, and then concentrated to dryness. The residue was taken into dichloromethane and filtered through a syringe filter. The filtrate was then treated with excess 4N HCl in dioxane, stirred for 15 minutes and then concentrated to dryness. The crude product was purified by reverse phase semi-prep HPLC to obtain the title product (43 mg, 47%); LCMS; m/z 376 (M, free amine); $^1$H NMR (400 MHz, DMSO); δ 1.63-1.70 (m, 2H), 1.74-1.82 (m, 1H), 2.21-2.29 (m, 3H), 2.42-2.45 (m, 3H), 2.62-2.73 (m, 2H), 2.85-2.89 (m, 1H), 4.85 (s, 1H), 6.91-6.96 (m, 4H), 6.98-7.01 (m, 2H), 7.36-7.40 (m, 2H), 8.21 (s, 1H).

EXAMPLE 15

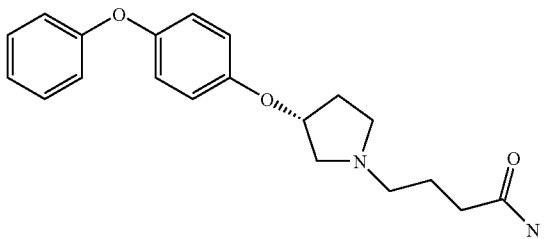

4-[(R)-3-(4-Benzyl-phenoxy)-pyrrolidin-1-yl]-butyramide: 4-[(R)-3-(4-Benzyl-phenoxy)-pyrrolidin-1-yl]-butyric acid methyl ester (200 mg, 0.566 mmol) was taken into 7N ammonia in methanol solution (5 mL) in a pressure tube. The reaction was sealed and heated at 100° C. for 48 h. The mixture was then cooled to room temperature and concentrated to dryness. The resulting residue was then purified by silica gel flash chromatography (20:1 silica ratio, eluted with a gradient of 10% methanol in dichloromethane to 15% methanol in dichloromethane) to obtain the title product (145 mg, 75%); LCMS; m/z 340 (M+1); $^1$H NMR (400 MHz, DMSO); δ 1.58-1.74(m, 3H), 2.04-2.08 (m, 2H), 2.19-2.24 (m, 1H), 2.33-2.41 (m, 3H), 2.54-2.58 (m, 1H), 2.61-2.65 (m, 1H), 2.78-2.82 (m, 1H), 3.85 (s, 2H), 4.77-4.80 (m, 1H), 6.68 (s, 1H), 6.78 (d, J=8.8, 2H), 7.11 (d, J=8.4, 2H), 7.17-7.22 (m, 3H), 7.25-7.29 (m, 1H).

Assays to Determine Potency of LTA4 Hydrolase Inhibitors (1) In vitro Assay Testing Inhibitory Activity Against Purified Recombinant Human $LTA_4$ Hydroase:

A human $LTA_4$ hydrolase full-length cDNA clone (NM_000895) was purchased from OriGene Technologies (Rockville, Md.). The gene was amplified by polmerase chain reaction and transferred via pDONR201 into the bacterial expression vector pDEST17 by recombination (both plasmids from Invitrogen, Carlsbad, Calif.). The resulting construct was transformed into *Escherichia coli* BL21-AI (Invitrogen), and expression was induced by chemical induction with arabinose. The recombinant enzyme was purified by chromatography on a FPLC system (Amersham Biosciences, Uppsala, Sweden) using immobilized metal affinity chromatography (Ni-NTA Superflow, Qiagen, Hilden, Germany) and anion exchange chromatography (MonoQ HR 10/10, Amersham Biosciences).

The compounds of the invention were incubated in a series of dilutions with 200 nM of recombinant enzyme in assay buffer (100 mM Tris-HCl, 100 mM NaCl, 5 mg/ml fatty-acid free BSA, 10% DMSO, pH 8.0) for 10 min at room temperature to allow binding between $LTA_4$ hydrolase and the inhibitors. $LTA_4$ was prepared by alkaline hydrolysis of $LTA_4$ methyl ester (Biomol, Plymouth Meeting, Pa., or Cayman Chemicals, Ann Arbor, Mich.). A solution of 10 µg of the ester was dried under a nitrogen stream and redissolved in 60 µl of a solution of 80% aceton and 20% 0.25 M NaOH. After incubation for 40 min at room temperature the resulting approximately 500 µM tock of $LTA_4$ was kept at −80° C. for no more than a few days prior to use.

Immediately before the assay, $LTA_4$ was diluted to a concentration of 10 µM in assay buffer (without DMSO) and added to the reaction mixture to a final concentration of 2 µM to initiate the enzyme reaction. After incubation for 120 sec at room temperature, the reaction was stopped by adding 2 volumes of chilled quenching buffer, containing acetonitrile with 1% acetic acid and 225 nM $LTB_4$-$d_4$ (Biomol). The samples were then kept at 4° C. over night to complete protein precipitation and centrifuged for 15 min at 1800 g. $LTB_4$ formed was measured by LC-MS/MS using $LTB_4$-$d_4$ as an internal standard and an external $LTB_4$ standard (Biomol) as reference. Briefly, the analyte was separated from $LTB_4$ isomers formed by spontaneous hydrolysis of $LTA_4$ using isocratic elution (modified protocol from Mueller et al. (1996), J. Biol. Chem. 271, 24345-24348) on a HPLC system (Waters, Milford, Mass.) and analyzed on a tandem quadrupole mass spectrometer (Waters). MRM transitions followed on 2 channels were 335.2>195.3 ($LTB_4$) and 339.2>197.3 ($LTB_4$-$d_4$). Based on the amounts of $LTB_4$ found at each inhibitor concentration, a dose-response curve was fitted to the data and an $IC_{50}$ value was calculated.

(2) Ex vivo Assay Testing Inhibitory Activity in Human Whole Blood After Stimulation with Calcium Ionophor:

Human blood was collected in heparin-containing Vacutainer tubes. For each sample, 200 µl of blood were dispensed into a pre-warmed plate and 188 µl of RPMI-1640 medium (Invitrogen) containing 20 µg/ml Indomethacin (Sigma, St. Louis, Mo.) were added. Then 4 µl of a series of compound dilutions (in DMSO) were added, followed by a 15 min incubation at 37° C. with gentle shaking. After that, blood samples were stimulated by adding Ionomycin (Calbiochem) to a final concentration of 20 µM. After another incubation at 37° C. for 30 min, samples were centrifuged for 5 min at 1800 g and 4° C. Supernatants were taken and $LTB_4$ concentrations were determined using a commercially available enzyme-linked immunoassay (R&D Systems, Minneapolis, Minn.) according to the manufacturer's instructions. Results obtained for different concentrations of hydrolase inhibitor were then used to fit a dose-response curve and calculate an $IC_{50}$ value.

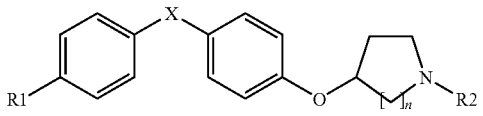

| Ex. | R1 | X | * | n | R2 | IC50(µM) (hLTA4H) | IC50(µM) (hWB) |
|---|---|---|---|---|---|---|---|
| 1 | H | CH2 | S | 1 | H | A | A |
| 2 | H | CH2 | R | 1 | H | A | A |
| 3 | H | O | N/A | 2 | H | A | A |
| 4 | H | CH2 | R | 1 | (CH2)3CO2H | A | ND |
| 5 | H | O | N/A | 2 | (CH2)2CO2H | A | ND |
| 6 | H | O | N/A | 2 | (CH2)3CO2H | A | ND |
| 7 | CF3 | O | N/A | 2 | H | A | ND |
| 8 | Ph | O | N/A | 2 | H | A | A |
| 9 | OCF3 | O | N/A | 2 | H | B | ND |
| 10 | Cl | O | N/A | 2 | H | A | ND |
| 11 | H | O | S | 1 | H | A | ND |
| 12 | H | O | S | 1 | (CH2)3CO2H | A | ND |

-continued

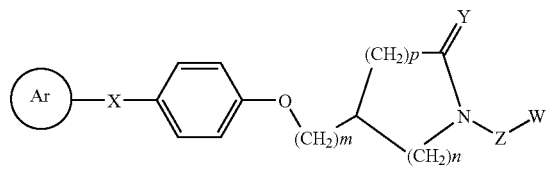

| Ex. | R1 | X | * | n | R2 | IC50(µM) (hLTA4H) | IC50(µM) (hWB) |
|---|---|---|---|---|---|---|---|
| 13 | H | O | S | 1 | (CH2)3CONH2 | A | ND |
| 14 | Cl | O | S | 1 | (CH2)3CO2H | A | ND |
| 15 | H | CH2 | S | 1 | (CH2)3CONH2 | A | ND |

A = <5 uM; B = 5-20 uM;
ND = Not Determined

We claim:
1. A compound of formula:

wherein
Ar is selected from the group consisting of phenyl and phenyl substituted with from one to three substituents independently selected from the group consisting of halogen, loweralkyl, loweracyl, loweralkoxy, fluoroloweralkyl, fluoroloweralkoxy, formyl, cyano, benzyl, benzyloxy, phenyl, substituted phenyl, heteroaryl, heterocyclylalkyl and nitro;

X is selected from the group consisting of O, $CH_2$, $CF_2$, C=O, and $CR^{1a}R^{1b}$;

$R^{1a}$ and $R^{1b}$ are selected from the group consisting of H and lower alkyl, or $R^{1a}$ and $R^{1b}$ taken together may form a 3-6 membered ring, which may optionally contain a heteroatom chosen from O, S, SO, $SO_2$, and $NR^{10}$;

$R^{10}$ is selected separately in each occurrence from the group consisting of H and lower alkyl;

m is zero, 1 or 2;

n is 1 or 2;

p is 1;

Y is selected from H,H; O; and H,$R^3$;

$R^3$ is lower alkyl;

Z is $(CH_2)_{1-10}$; in which one or two ($CH_2$) may optionally be replaced by a —O—, —$NR^{10}$—, —SO—, —$S(O)_2$—, —C(=O)— or —C=O(NH)—, provided that said —O—, —$NR^{10}$—, —SO—, —$S(O)_2$—, —C(=O)— or —C=O(NH)— are not at the point of attachment to nitrogen and are separated by at least one —$(CH_2)_2$—;

W is carboxyl or carboxamido; and $R^4$ is selected from the group consisting of H and lower alkyl.

2. A compound according to claim 1, wherein m is zero of formula:

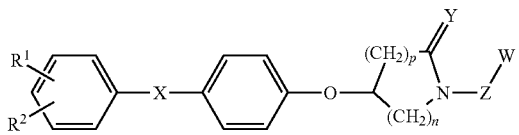

wherein
R¹ or R² or are independently chosen from hydrogen, halogen, loweralkyl, loweracyl, loweralkoxy, fluoroloweralkyl, fluoroloweralkoxy, formyl, cyano, benzyl, benzyloxy, sulphonamide, amido, phenyl, substituted phenyl, heteroaryl, heterocyclylalkyl and nitro; or R¹ and R² taken together may form a 5-6 membered ring, which may optionally contain an oxygen.

3. A compound according to claim 2, wherein
n is 1;
Z is $(CH_2)_{1-10}$.

4. A compound according to claim 3, wherein Y is H,H of formula:

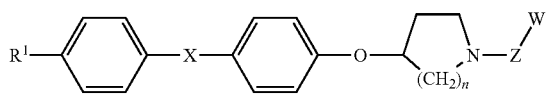

wherein
R¹ is chosen from hydrogen, trifluoromethyl, $(CF_3)_2CHCH_2$—, methoxy, halogen, phenyl, cyano, and nitro;
X is chosen from —O— and —$CH_2$—;
Z is $(CH_2)_{1-3}$; and
W is COOH.

5. A pharmaceutical composition comprising a pharmaceutically acceptable carrier and a therapeutically effective amount of at least one compound according to claim 1.

6. A compound according to claim 2, wherein n is 2 and Z is $(CH_2)_{1-10}$.

7. A compound according to claim 6, wherein Y is H,H of formula:

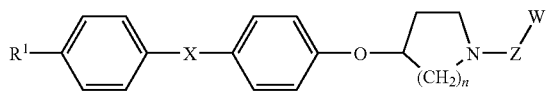

wherein
R¹ is chosen from hydrogen, trifluoromethyl, $(CF_3)_2CHCH_2$—, methoxy, halogen, phenyl, cyano, and nitro;
X is chosen from —O— and —$CH_2$—;
Z is $(CH_2)_{1-3}$; and
W is COOH.

8. A compound according to claim 2 of formula:

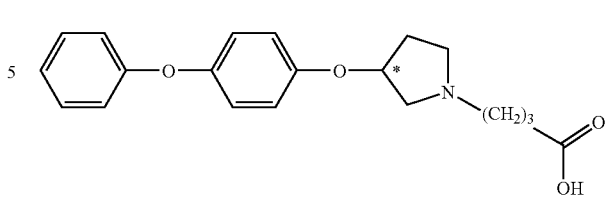

wherein R¹ and R² are H; X is O; m is 0; Y is H,H; n is 1; Z is —$(CH_2)_3$—, W is COOH, and the asterisk represents a chiral center having a (R) configuration.

9. A compound according to claim 2 of formula:

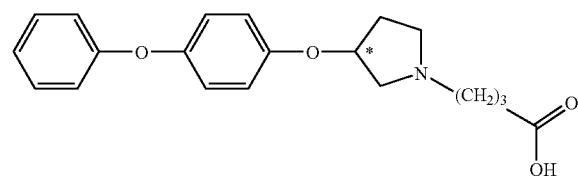

wherein R¹ and R² are H; X is O; m is 0; Y is H,H; n is 1; Z is —$(CH_2)_3$—, W is COOH, and the asterisk represents a chiral center having a (S) configuration.

10. A compound according to claim 2 of formula:

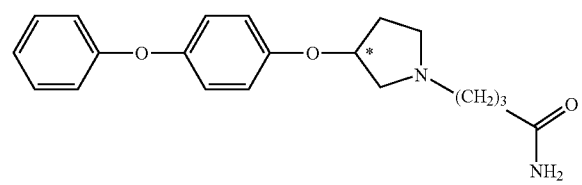

wherein R¹ and R² are H; X is O; m is 0; Y is H,H; n is 1; Z is —$(CH_2)_3$—, W is $CONH_2$, and the asterisk represents a chiral center having a (S) configuration.

11. A compound according to claim 2 of formula:

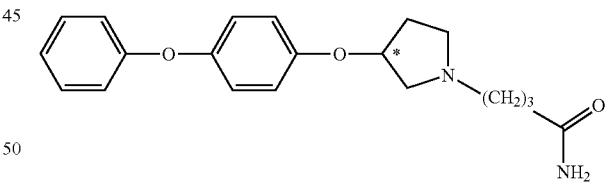

wherein R¹ and R² are H; X is O; m is 0; Y is H,H; n is 1; Z is —$(CH_2)_3$—, W is $CONH_2$, and the asterisk represents a chiral center having a (R) configuration.

* * * * *